United States Patent
Onwunaka et al.

[11] Patent Number: 5,266,669
[45] Date of Patent: Nov. 30, 1993

[54] SOFTENING NON-SWELLING POLYURETHANE

[75] Inventors: Theophilus O. Onwunaka, Midvale; James M. Lambert, Sandy, both of Utah

[73] Assignee: Becton, Dickinson and Company, Franklin Lakes, N.J.

[21] Appl. No.: 966,233

[22] Filed: Oct. 26, 1992

[51] Int. Cl.[5] ............................................... C08G 18/38
[52] U.S. Cl. ...................... 528/28; 528/67; 528/76; 528/78
[58] Field of Search .................. 528/28, 67, 76, 78

[56] References Cited
U.S. PATENT DOCUMENTS 4,822,827 4/1989 Bonk et al. .

*Primary Examiner*—Maurice J. Welsh
*Attorney, Agent, or Firm*—Richard E. Brown

[57] ABSTRACT

A non-yellowing, elastomeric polyurethane is made from a non-aromatic diisocyanate, a diol chain extender, a polyglycol and an aminodiol chain extender. The polyurethane is stable to sterilizing radiation, is made without any processing aids or toxic catalysts, and softens without swelling up to 95% when contacted with an aqueous liquid.

10 Claims, No Drawings

SOFTENING NON-SWELLING POLYURETHANE

BACKGROUND OF THE INVENTION

1. Field of the Invention

This invention relates to thermoplastics and more particularly relates to elastomeric polyurethanes and medical articles therefrom.

2. Background of the Invention

Polyurethanes possess an outstanding balance of physical and mechanical properties and superior blood compatibility compared to other polymers such as silicone rubber, polyethylene, polyvinyl chloride and perfluorinated polymers. As a result, they have come to the fore as the preferred polymeric biomaterials for fabrication of various medical device components. Some important device applications for polyurethanes include peripheral and central venous catheters, coatings for heart pacemaker leads and the Jarvik heart.

As known in the art, polyurethanes are synthesized from three basic components, a diisocyanate, a polyglycol and an extender, usually a low molecular weight diol, diamine, or water. If the extender is a diol, the polyurethane consists entirely of urethane linkages. If the extender is water or diamine, both urethane and urea linkages are present and the polyurethane is termed a polyurethaneurea.

Polyurethanes develop microdomains conventionally termed hard segments and soft segments, and as a result are often referred to as segmented polyurethanes. The hard segments form by localization of the portions of the polymer molecules which include the isocyanate and extender components and are generally of high crystallinity. The soft segments form from the polyglycol portions of the polymer chains and generally are either noncrystalline or of low crystallinity. One of the factors which determines the properties of the polymer is the ratio of hard and soft segments. In general, the hard segment contributes to hardness, tensile strength, impact resistance, stiffness and modulus while the soft segment contributes to water absorption, elongation, elasticity and softness.

Polyurethanes chain extended with diols have been extensively studied for biomedical application. Exemplary of important diol extended polyurethanes are: VIALON TM (Becton, Dickinson and Company) PELLETHANE TM (Upjohn Chemical Co.,) and TECOFLEX TM (Thermedics Inc.) These proprietary products typically have good blood compatibility, but, with the exception of VIALON TM, generally require processing additives such as antioxidants and detackifiers, a potential disadvantage for use in biomedical articles. They are, however, thermoplastic and therefore may be extruded and injection molded.

U.S. Pat. No. 4,202,957 to Bonk et al. discloses a polyurethane from a diisocyanate, an extender and a particular polyoxyethylene-polyoxypropylene glycol which is stable up to 450° F. and therefore is melt processable without decomposition. In U.S. Pat. No. 4,822,827, Bonk et al. further improve heat stability for thermoplastic processing by including a cycloalkane diol extender in the formulation.

A softening and swelling catheter fabricated of a polyurethane synthesized from polyethyleneoxide soft segment is disclosed in U.S. Pat. No. 5,061,254 to Karakelle et al. of common assignee herewith.

A multilumen catheter marketed under the trade name FLEXTIP TM by Arrow International Corp., Wilmington, Del. and disclosed by Howes in U.S. Pat. No. Re. 31,873 and by Botterbusch et al. in U.S. Pat. No. 5,004,456 consists of a relatively soft distal end segment intended for insertion into a body cavity and a relatively hard rigid portion joined thereto by heat and/or pressure. The catheter segments are polyurethanes from aliphatic or aromatic diisocyanates.

While significant improvement in catheter performance has resulted from the above disclosures, there remains a need for a radiation stable polyurethane having the blood compatibility necessary for catheter manufacture which is stiff when dry for catheter insertion but which becomes soft and pliable for positioning and indwelling. The present invention addresses this need.

SUMMARY OF THE INVENTION

A melt processable radiation stable, elastomeric polyurethane is synthesized from a non-aromatic diisocyanate, a nonhydrophilic polyglycol and a mixture of a diol chain extender and an aminodiol chain extender. The polyurethane has a hard segment of about 50 to 70% and a softening ratio of up to 95% with substantially no swelling after about 10 minutes contact with an aqueous liquid.

The preferred diisocyanate is 4,4'-dicyclohexyl methanediisocyanate (HMDI) and the preferred soft segment polyol is polytetramethylene ether glycol (PTMEG). Preferred extenders are 1,4-butanediol (BDO) and N butyl diethanolamine (BDA).

The polyurethane may be fabricated into devices of any desired shape. Preferred devices are medical devices, most preferably a catheter.

A catheter fabricated from the polyurethane of the invention is initially stiff but softens up to 95% without swelling compared to softening of about 60% for catheters of the prior art. The high initial bend force provides stiffness which is highly advantageous for catheter insertion in a patient. The high softness after contact with a body fluid provides flexibility which aids positioning and reduces the risk of vessel wall perforation. The non-swellability feature of the disclosed catheter is particularly important for central venous applications. In such applications, the catheter is placed close to the heart and is subject to continual motion due to the beating of the heart. As a result, a problem in central venous catheterization has been irritation of the vessel wall due to continual rubbing by the catheter wall. This condition can lead to phlebitis and hemorrhage. Swellable catheters increase in lumen size, bring catheter and vessel walls closer together and exacerbate this problem, or even increase the possibility of occluding the vessel entirely. In peripheral catheterization these events are not a serious problem because the many smaller blood vessels in the catheterized area are quickly able to bypass the affected area. The polyurethane of the invention offers advantages over commercially used catheter materials such as TECOFLEX TM or PELLETHANE TM because excellent tensile strength with concomitant softening is achieved by a process which is free of potentially leachable toxic catalysis or processing aids. In contrast to prior art catheters, the initial stiffness combined with the high softening after insertion allows a catheter to be manufactured as a one-piece unit with no joints which may come apart during use and leave a catheter section free inside a patient.

DETAILED DESCRIPTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments described. The scope of the invention will be measured by the appended claims and their equivalents.

In accordance with the present invention, a radiation stable, melt processable polyurethane having a desirable ratio of stiffness when dry and softness without swelling when wet is achieved in a catalyst free process using a mixture of nonhydrophilic soft segment polyols and a mixture of chain extenders. The polyurethanes are useful for medical device components such as catheters, adapters, intravenous tubing, needle hubs, lancets and the like.

Polyisocyanates useful in the present invention are aliphatic or alicyclic isocyanates. Representative of suitable isocyanates are aliphatiac diisocyanates such as 1,6-hexamethylene diisocyanate (HDI), trimethylhexamethylene diisocyanate (TMDI) and 1,10d-ecamethylene diisocyanate. Preferred isocyanates are alicyclic diisocyanates such as isophorone diisocyanate. The most preferred isocyanate is HMDI.

Stiffness, softness and swelling may be controlled by the choice of the soft segment material and the ratio of soft segment to hard segment. The soft segment preferably is substantially non-hydrophilic since any appreciable water absorption causes swelling. In the present disclosure, the term non-hydrophilic means 30% or less, preferably 15% or less by weight water absorption. Suitable soft segments of the polyurethanes of the instant invention may be a non-hydrophilic polycarbonate, polyester, polyether or silicone glycol having a molecular weight of 500 to 8000. Preferred polyglycols are substantially non-hydrophilic polyether glycols. The preferred polyetherglycol for the soft segment is PTMEG having a molecular weight of 500 to 3000. The most preferred soft segment is a mixture of two or more PTMEGs of molecular weight of about 1000 to 2000 and about 2% by weight water absorption. These products are available commercially under the trade names POLYMEG TM (Quaker Oats Co., Chemical Division) and TERETHANE TM (Dupont) respectively.

One chain extender component may be any branched or unbranched diol of up to 12 carbon atoms. Representative nonlimiting examples of chain extenders are ethylene glycol, diethylene glycol, triethylene glycol, 1,2-propanediol, 1,3-propanediol, 1,6-hexanediol, 1,8-octanediol, bis hydroxymethyl cyclohexane and hydroquinone dihydroxyethyl ether. The preferred extender is BDO.

A coextender component is an amino diol, preferably a tertiary amino diol. Suitable coextenders are bis hydroxyalkyl tertiary amines having the following structure:

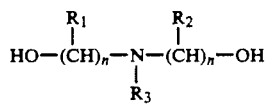

In this structure, $R_1$ and $R_2$ may independently be hydrogen or alkyl, $R_3$ may be alkyl and n may be 2 to 6 wherein the term alkyl means about 1 to 18 carbon atoms. Suitable tertiary amines are, for example, N-methyldiethanolamine, N-dodecyldiethanolamine, N-octadecyldiethanolamine and N-ethyldiisopro panolamine. The preferred bis hydroxyalkyl tertiary amine is BDA. This product is available from Union Carbide Corporation, (Bound Brook, N.J.) and the invention will hence forth be described in terms of the preferred BDA.

The ratio of the diol and aminodiol components of the extender may be about 1:99 to 99:1, respectively. A preferred ratio is about 10:1, most preferably about 5:1.

In the present invention, the aminodiol coextender component promotes the reaction of the isocyanate groups with hydroxyl groups of the extender and polyglycol. This component is inherently non-toxic, and, because it becomes part of the polymer chain, is not a true catalyst. Being part of the polymer chain, it is non-leachable. The hard segment includes the isocyanate, the diol extender and the aminodiol extender and may be from about 50 to 70, preferably 55 to 65% by weight of the total polymer weight. The soft segment includes the polyglycol and may be about 70 to 50, preferably about 45 to 35% by weight. An isocyanate index of 1.0 to 1.1, preferably about 1.02, may be used. From the desired hard segment content of the product, the isocyanate index, the ratio of diol to aminodiol and the molecular weights of the components, the proportions of the reagents to be used may readily be calculated.

The polyurethanes of the invention may be prepared by a process generally referred to as bulk or one-shot synthesis. In a conventional one-shot process, all of the ingredients are combined, usually with stirring, at the beginning of the process in the presence of a polymerization catalyst, usually an organometallic compound. It has now been discovered that polyurethanes which are melt processable may be obtained by a simple one-pot procedure without an organometallic catalyst. Conventional organometallic catalysts, such as dibutyl tin dilaurate and stannous octoate, are toxic and leachable and may cause deleterious effects in medical device elements contemplated for contact with a patient's body fluid.

In one preferred process of the invention, conventional polymerization equipment is charged with a mixture of the polyglycol and extenders in proportions predetermined in accordance with the desired hard segment-soft segment ratio. With vigorous stirring, the diisocyanate may be added all at once. If the reaction does not start spontaneously, the mixture may be heated sufficiently to induce an exothermic reaction. The reaction mixture may be stirred vigorously until the exotherm is complete and the temperature begins to drop off, generally for about 1 to 5 minutes. The clear homogeneous melt, while still hot, may advantageously be removed from the reactor prior to curing.

Any conventional method may be used to effect curing. Preferably, the melt is simply set aside for a suitable time and temperature, as, for example, from ambient to about 130° C. and for about 1 hour to 20 days, to be cured by atmospheric moisture.

Any polymerization equipment or technique which provides a clear melt at the conclusion of the exotherm is contemplated to fall within the scope of the invention. Preferred equipment includes a multi-paddle shaft driven at high rotation rate by a motor. Exemplary of such a system is the Fluidyne Model 63014 MICRO-SHOT TM Elastomer Processing system.

The polyurethane resins of the invention may be fabricated into film, tubing and other forms by conventional thermoplastic fabricating techniques including melt casting, extrusion, molding, etc. The resin may have incorporated therein, as desired, conventional stabilizers and radiopaque materials such as barium sulfate and the like. The amounts of these materials will vary depending upon the application of the polyurethane, but they are typically present in amounts ranging from about 0.1 to 40 weight percent of the polymer.

The preferred article of the invention is a catheter, most preferably a multilumen catheter. While the number of lumens is limited only by the extrusion die used, the most preferred catheter of the invention is trilumen.

Tensile strength is a measure of the force, generally given in pounds per square inch (psi), required to break a polymer. Elongation is a measure of the ability of a polymer to stretch without breaking, and is generally reported as a percentage of an initial value. The term modulus defines the force, in psi, required to stretch a polymer to a given percentage of the elongation.

The tensile, elongation and modulus of the polyurethane of the invention may be measured by ASTM procedure D638 using an Instron Universal Testing Instrument, Model 1122. Representative polymers of the invention are given, along with their physical properties in Table I.

When tested for stiffness and softening by the conventional procedure of Example III, the catheter of the invention had an initial (i.e., when dry) bend force of about 100 to 300, preferably about 150 to 250, most preferably about 180 to 200 g. After contact with normal saline at 37° C. for various time periods, the catheters had softened up to 95% at equilibrium (after about 30 minutes) to a bend force of 40, preferably about 25, most preferably about 17 g. Further, the softening is very rapid and had reached about 90% of its equilibrium level after only 10 minutes, about the length of time required for insertion and positioning by a skilled practitioner.

In comparison, a catheter from the polyurethane disclosed in the aforementioned U.S. Pat. No. 4,202,957 could not be processed by extrusion into a suitable catheter tube. A catheter from the polyurethane of the aforementioned U.S. Pat. No. 4,822,827, was very stiff when dry and was substantially non-softening on immersion in saline. In addition, it was very brittle making it potentially dangerous for in vivo use.

Swelling of polyurethanes is well known to be due to water absorption resulting from the presence of one or more hydrophilic components. Swelling may be determined by the procedure of Example IV. Softening and swelling data for the polyurethane of the invention and the polyurethanes of U.S. Pat. Nos. 4,202,957 and 4,822,827 are given in Table I.

It has been found that the polyurethane of the invention is substantially non swelling if the water absorption is 10%, preferably 5% by weight or less.

TABLE I

| Formulation | Tensile (psi) | Modulus (psi) | Elongation % | Bend Force dry | Bend Force wet | Softening % | Swelling % |
|---|---|---|---|---|---|---|---|
| IA | 4400 | 1900 | 400 | 188 | 17 | 91 | 0 |
| IB | 800 | 600 | 390 | 18 | 11 | 39 | 0 |
| USP'957 | non-extrudable | | N/A | N/A | N/A | N/A | N/A |
| USP'827 | 1473 | | 5 | 1999 | 2400 | 0 | 0 |

It is seen that formulation IA of the invention has high initial (dry) bend force to aid insertion, and softens up to 95% when wet to aid positioning. It is also seen that the polyurethane of the invention does not swell and therefore does not change in size. In contrast, the polyurethanes of the prior art closest in composition to the polyurethane of the invention are either non-extrudable into catheter tubing or are up to 10 fold stiffer when dry, without softening when wet. It is also seen that a polyurethane of about 40% hard segment (IB) is substantially soft even when dry.

EXAMPLE I

General Procedure for Synthesis

The polyols and extenders were mixed thoroughly and warmed to 60° C. The diisocyanate or mixture thereof at 50° C. was poured into the stirring mixture. A slight exotherm resulted. The mixture was then gradually heated with stirring until an exotherm to about 135° C. took place. The viscous liquid was cured in an oven at 125° C. for 1 hour.

| Formulation IA: (60% hard segment) | |
|---|---|
| HMDI | 1.02 eq. |
| PTMEG T 1000 | 0.155 eq. |
| PTMEG T 2000 | 0.038 eq. |
| BDO | 0.729 eq. |
| BDA | 0.081 eq. |
| Comparative Formulation IB (40% hard segment) | |
| HMDI | 1.02 eq. |
| PTMEG T 1000 | 0.327 eq. |
| PTMEG T 2000 | 0.080 eq. |
| BDO | 0.533 eq. |
| BDA | 0.060 eq. |
| Formulation IC (60% hard segment) | |
| TMDI | 1.02 eq. |
| PTMEG T 1000 | 0.131 eq. |
| PTMEG T 2000 | 0.032 eq. |
| BDO | 0.752 eq. |
| BDA | 0.084 eq. |

EXAMPLE II

Polymer Compounding and Extrusion

Cured slabs from Example IA and IB were sliced with a band saw and chipped using conventional grinding and chipping machines before drying for 48 hours. The pellets were extruded into 7 French monolumen tubings with a Brabender PLASTICORDER ™ torque rheometer using a ¾ in. single screw attachment with an L/D of 25/1 and compression of 3:1.

The extruded tubings were used to determine the softening profile of the polyurethanes.

The extrusion conditions used are given in Table II below.

TABLE II

| | Ex IA | IB | USP'957* | USP'827 |
|---|---|---|---|---|
| Zone 1 | 145° C. | 145 | | 120 |
| 2 | 145 | 145 | | 150 |
| 3 | 210 | 195 | | 195 |
| Die | 215 | 200 | | 215 |
| Torque | 40–50 | 40–50 | | 50–60 |
| RPM | 10–15 | 10–15 | | 10–15 |

*USP'957 could not be extruded: Extrusion temperatures were varied from 100–160° C. (Zone 1 & 2), 150–250 (Zone 3) with no acceptable extrusions produced. Material either foamed (degraded) at higher temperatures or produced very high (unacceptable) torques and freeze fractures at the lower temperatures.

EXAMPLE III

Determination of Bend Force and Percent Softening

Extruded 7 French monolumen catheter tubings were conditioned for 48 hours at 23° C. and relative humidity of 50%. Initial bend forces were determined after conditioning for 48 hr. at 37° C. and bend forces at equilibrium (about 30 min.) were determined after soaking at 37° C. in normal saline with an Instron Universal Testing Machine, Model 1122, equipped with an environmental chamber maintained at 37° C. and 100% relative humidity.

EXAMPLE IV

Determination of Water Absorption and Swelling

An extruded 7-French monolumen catheter of the invention was dipped into water at 37° C., withdrawn from the water at a predetermined time, and the inside diameter was measured and compared with the inside diameter of the dry catheter. Water absorption was measured by weighing dry and after soaking for 20 hours.

What is claimed is:

1. A melt processable elastomeric polyurethane comprising a product from the reaction of a non-aromatic diisocyanate, a diol chain extender, a tertiary aminodiol chain extender and a polyglycol, said polyurethane being substantially nonswelling, having a hard segment of about 50 to 70%, and a softening ratio of up to 95% after contact with an aqueous liquid.

2. The polyurethane of claim 1 wherein said polyglycol is selected from the group consisting of a polyester glycol, a polyether glycol, a silicone glycol and a polycarbonate glycol.

3. The polyurethane of claim 1 wherein said diisocyanate is selected from the group consisting of an aliphatic diisocyanate and an alicyclic diisocyanate.

4. A melt processable, elastomeric polyurethane comprising a product from the reaction of an alicyclic diisocyanate, an aliphatic diol chain extender, a polytetramethylene ether glycol and a bis hydroxyalkyl tertiary amine, said polyurethane being substantially nonswelling, having a hard segment of 50 to 70% and a softening ratio of up to 95% when contacted with an aqueous liquid.

5. The polyurethane of claim 4 wherein said alicyclic diisocyanate is selected from the group consisting of isophorone diisocyanate and 4,4'-dicyclohexylmethane diisocyanate.

6. The polyurethane of claim 4 wherein said diol chain extender is selected from the group consisting of ethylene glycol, diethylene glycol, triethylene glycol 1,2-propanediol, 1,3-propanediol, 1,6- hexanediol, 1,8-octanediol, and 1,4-butanediol.

7. The polyurethane of claim 4 wherein said bis hydroxyalkyl tertiary amine is selected from the group consisting of N-methyldiethanolamine, N-dodecyldiethanolamine, N-octadecyldiethanolamine, N-ethyldiisopropanolamine and N-butyldiethanolamine.

8. The polyurethane of claim 4 further including a radiopaque agent.

9. A melt processable elastomeric polyurethane comprising the reaction product of 4,4'-dicyclohexylmethane diisocyanate, 1,4-butanediol, N-butyldiethanolamine and at least two polytetramethylene ether glycols of different molecular weight, said polyurethane being substantially nonswelling, having a hard segment of about 55 to 65% and a softening ratio of up to 90% when contacted by an aqueous liquid.

10. A catheter fabricated from the polyurethane of claim 1.

* * * * *